United States Patent
Wu et al.

(10) Patent No.: US 7,645,879 B2
(45) Date of Patent: Jan. 12, 2010

(54) PHOTOSENSITIZER DYE

(75) Inventors: Chun-Guey Wu, Hualien County (TW);
Chia-Yuan Chen, Chiayi (TW);
Shi-Jhang Wu, Taipei County (TW);
Jheng-Ying Li, Taoyuan County (TW)

(73) Assignee: National Central University, Taoyuan (TW)

( * ) Notice: Subject to any disclaimer, the term of this patent is extended or adjusted under 35 U.S.C. 154(b) by 0 days.

(21) Appl. No.: 12/125,939

(22) Filed: May 23, 2008

(65) Prior Publication Data

US 2009/0209761 A1    Aug. 20, 2009

(30) Foreign Application Priority Data

Feb. 19, 2008    (TW) .............................. 97105782 A

(51) Int. Cl.
*C07F 15/00*    (2006.01)
*B01J 31/12*    (2006.01)

(52) U.S. Cl. ......................................... 546/2; 502/167
(58) Field of Classification Search ..................... 546/2; 502/167
See application file for complete search history.

(56) References Cited

U.S. PATENT DOCUMENTS 7,321,037 B2    1/2008    Wu et al.

FOREIGN PATENT DOCUMENTS

WO    WO 2007/091525    *    8/2007

OTHER PUBLICATIONS

Article titled "A low cost, high efficiency solar cell based on dye-sensitized colloidal $TiO^2$ films", authored by O'Regan, et al., adopted from Nature 1991, vol. 353, pp. 737-740.
Article titled "Conversion of light to electricity by cis-x2bis(2, 2'-bipyridyl-4, 4'-dicarboxylate)ruthernium(II) charge-transfer sensitizers (x=$Cl^-$, $Br^-$, $I^-$, $Cn^-$, and $Scn^-$) on nanocrystalline $TiO^2$ electrodes", authored by Nazeeruddin, et al., adopted from Journal American chemcial society, 1993, 115, pp. 6382-6390.
Article titled "Engineering of efficient panchromatic sensitizers for nanocyrstalline $TiO^2$-based solar cells", authored by Nazeeruddin, et al., adopted from Journal American chemical society, 2001, 123, pp. 1613-1624.
Article titled "Stable new sensitizer with improved light harvesting for nanocyrsatllline dye-sensitized solar cells", authored by Zakeeruddin, et al., adopted from Advanced materials, 2004, 1, pp. 1806-1811.
Article titled "Combined experimental and DFT-TDDFT computational study of photoelectrochemical cell ruthenium sensitizers", authored by Nazeeruddin, et al., adopted from Journal American chemical society, 2005, 127, pp. 16835-16847.
Article titled "A high molar extinction coefficient sensitizer for stable dye-sensitized solar cells", authored by Wang, et al., adopted form Journal American chemical society, 2005, 127, pp. 808-809.
Article titled "A ruthenium complex with superhigh light-harvesting capacity for dye-sensitize dsolar cells", authored by Chen, et al., adopted from Angew. Chem. Int. Ed., 2006, 45, 5822-5825.
Article titled "A new route to enhance the light-harvesting capability of ruthenium complexes for dye-sensitized solar cells", authored by Chen, et al., adopted from Advance material, 2007, 19, pp. 3888-3891.
Article titled "High-efficiency and stable mesoscopic dye-sensitized solar cells based on a high molar extinction coefficient ruthenium sensitizer and nonvolatile electrolye", authored by Kuang, et al., adopted from Advance materials, 2007, 19, 1133-1137.

* cited by examiner

*Primary Examiner*—Charanjit S Aulakh
(74) *Attorney, Agent, or Firm*—Jianq Chyun IP Office

(57) ABSTRACT

A photosensitizer dye is provided. The photosensitizer dye is a Ru complex as formula (1):

Formula (1)

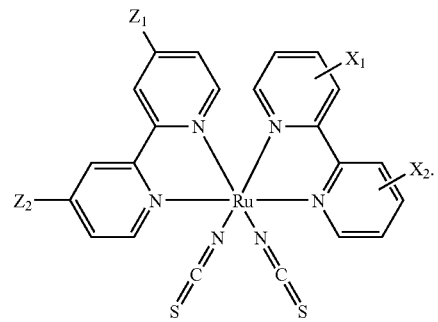

1 Claim, 4 Drawing Sheets

PHOTOSENSITIZER DYE

CROSS-REFERENCE TO RELATED APPLICATION

This application claims the priority benefit of Taiwan application serial no. 97105782, filed on Feb. 19, 2008. The entirety of the above-mentioned patent application is hereby incorporated by reference herein and made a part of specification.

BACKGROUND OF THE INVENTION

1. Field of Invention

The present invention relates to a solar cell material. More particularly, the present invention relates to a photosensitizer dye applicable in dye-sensitized solar cells.

2. Description of Related Art

Not only the supply of fossil fuels is expected to run out in an imminent future, the high consumption of fossil fuels poses an alarming threat to the environment and public health due to their poisonous emissions into the atmosphere. Accordingly, scientists are constantly in the search and the development of renewable and sustainable energy sources. Currently, the renewable energy sources include: solar energy, wind energy, hydraulic energy, tidal energy, geothermal energy, biomass energy, etc. Among the various types of energy sources, solar energy has been the most pursued due to its abundant supply. Further, the application of solar energy is not limited by physical environment or geomorphology, and solar energy can be directly converted to electricity with the appropriate equipments and apparatuses, which are known as solar cells (or photovoltaic).

Recently, Grätzel and O'Regan have proposed a new type of solar cell known as dye-sensitized solar cells (DSCs), which offer many advantageous prospects, such as, high photoelectric conversion efficiency, high transparency, the capability of displacing of different colors by the cell, and flexibility in which the cell is capable folding up or bending. Hence, the dye-sensitized solar cells are well received in the industry. Typically a dye-sensitized solar cell is constituted with four parts including an anode/cathode for providing a channel of current flow, a semiconductor material (such as, titanium dioxide $TiO_2$ or zinc oxide ZnO) for accepting and transporting electrons, a dye layer attached onto the surface of the semiconductor material by a self-assembly manner, and an electrolyte for transporting holes. The materials used at each part and the interface between each part in the dye-sensitized solar cell play important roles on influencing the photoelectrical conversion efficiency of the cell. Most particularly, wherein the dye used in the photosensitizer layer is the most critical in influencing the efficiency of a dye-sensitized solar cell.

Accordingly, to identify a dye that has a high absorption coefficient for enhancing the photoelectrical conversion efficiency of a dye-sensitized solar cell has been enthusiastically pursued in the dye-sensitized solar cell industry.

SUMMARY OF THE INVENTION

In view of the foregoing, the present invention provides a photo sensitizer dye, wherein the photoelectric conversion efficiency of a dye-sensitized solar cell using the dye is enhanced.

The present invention provides a photosensitizer dye, wherein the photosensitizer dye is a ruthenium (Ru) complex represented by the following general formula (1):

Formula (1)

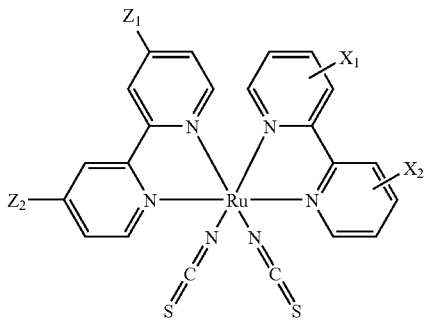

wherein $X_1$ represents one of the following formulas (2) to (18), and $X_2$ represents hydrogen (H) or both $X_2$ and $X_1$ represent one of the following formulas (2) to (18).

Formula (2)

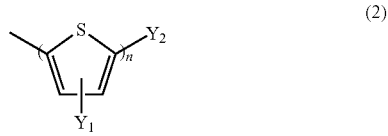
(2)

(3)
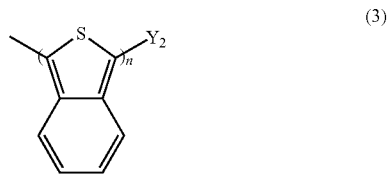

(4)
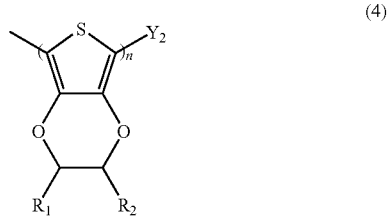

(5)
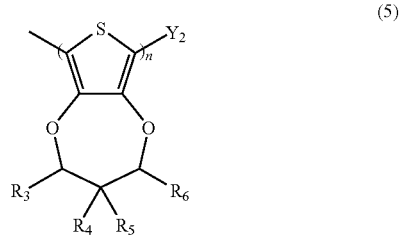

(6)
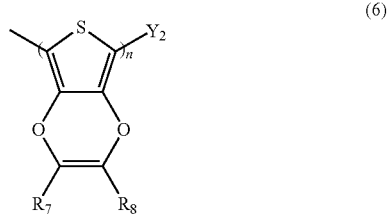

-continued
(7)
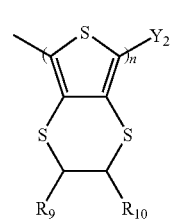
(8)
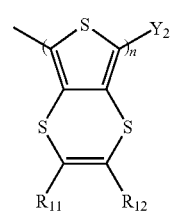
(9)
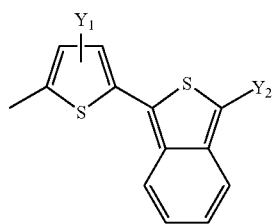
(10)
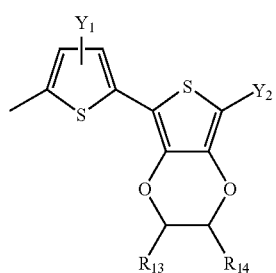
(11)
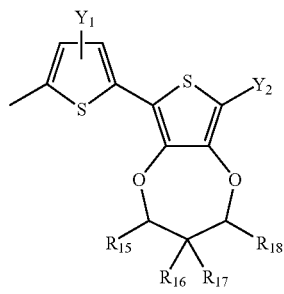
(12)
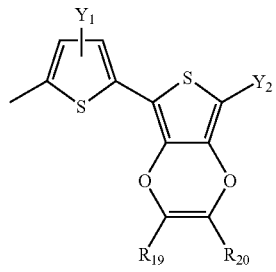
-continued
(13)
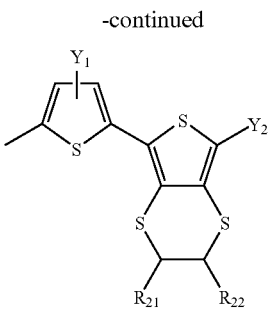
(14)
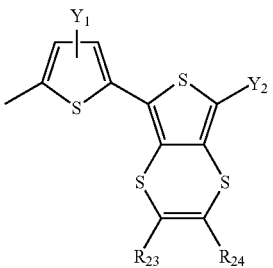
(15)
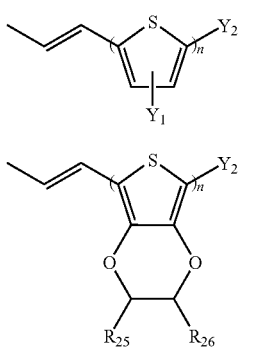
(16)
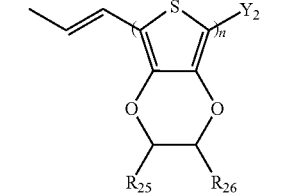
(17)
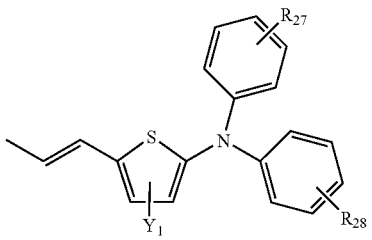
(18)
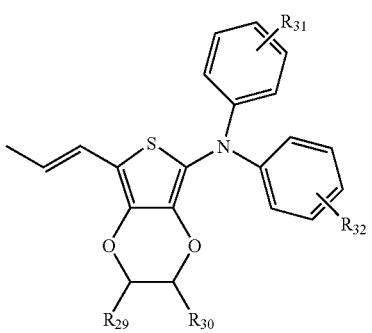
wherein $R_1$, $R_2$, $R_3$, $R_4$, $R_5$, $R_6$, $R_7$, $R_8$, $R_9$, $R_{10}$, $R_{11}$, $R_{12}$, $R_{13}$, $R_{14}$, $R_{15}$, $R_{16}$, $R_{17}$, $R_{18}$, $R_{19}$, $R_{20}$, $R_{21}$, $R_{22}$, $R_{23}$, $R_{24}$, $R_{25}$, $R_{26}$, $R_{27}$, $R_{28}$, $R_{29}$, $R30$, $R_{31}$ and $R_{32}$ independently represents one of H, $C_mH_{2m+1}$ (m=1 to 15), $OC_pH_{2p+1}$ (p=1 to 15), and n=1 to 4, and wherein $Y_1$ and $Y_2$ independently represent one of formulas (19) ~ (34).

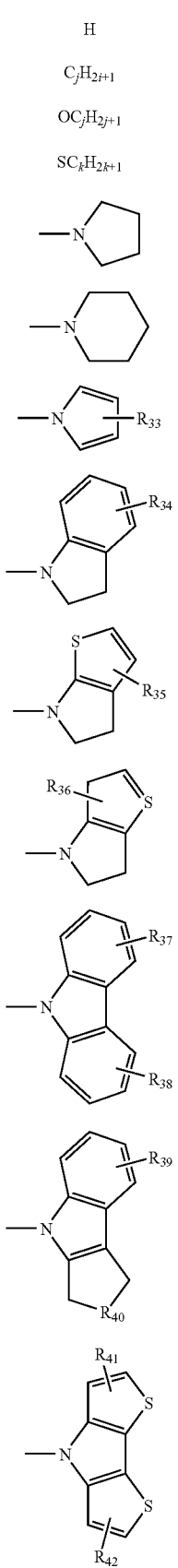
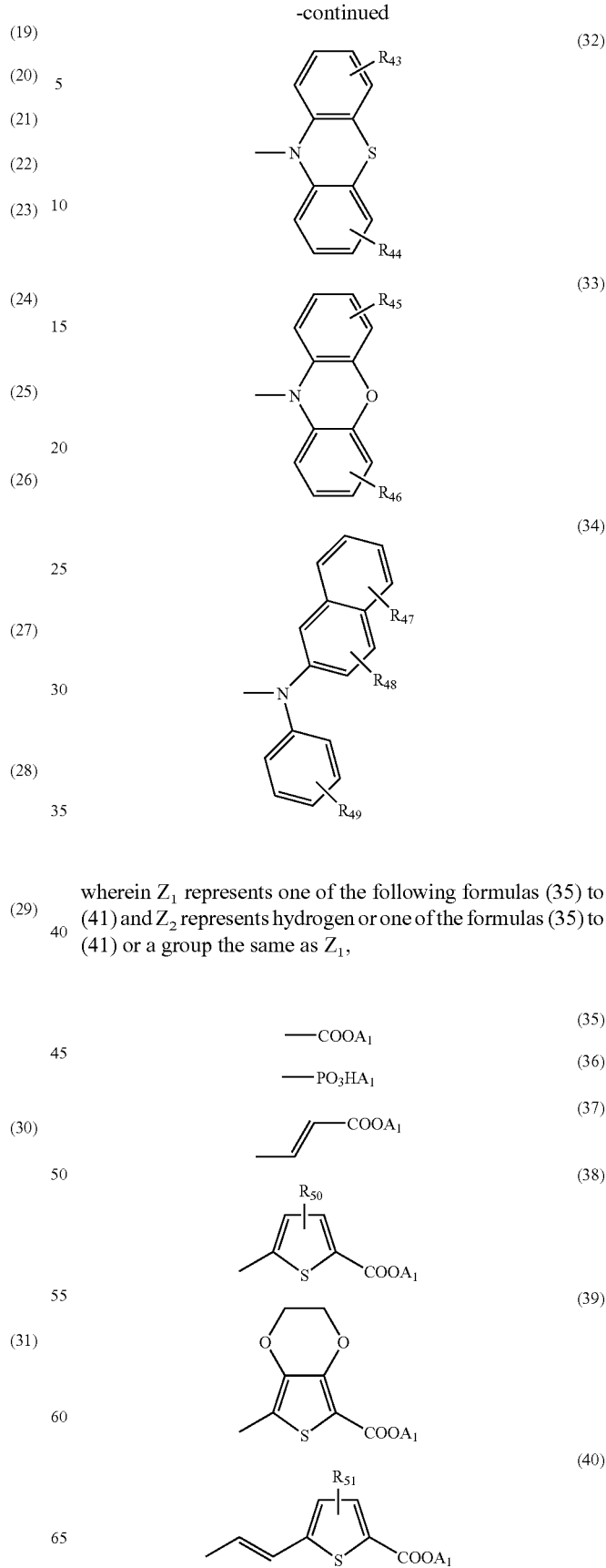
wherein $Z_1$ represents one of the following formulas (35) to (41) and $Z_2$ represents hydrogen or one of the formulas (35) to (41) or a group the same as $Z_1$, -continued (41)

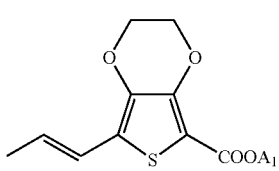

wherein A1 represents hydrogen (H), lithium (Li), sodium (Na), potassium (K) or tetra-alkyl ammonium groups as in the following general formula (42), (42)

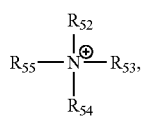

wherein $R_{52}$, $R_{53}$, $R_{54}$ and $R_{55}$ independently represents H or $C_mH_{2m+1}$ (m=1 to 15). When $Z_1$ and $Z_2$ both represent formula (35) and $X_1$ represents one of the formulas (2) to (4) and $X_2$ represents hydrogen, $Y_2$ does not represent one of thee formulas (19) to (21). When $Z_1$ and $Z_2$ both represent formula (35), and $X_1$ and $X_2$ both represent one of the formulas (2) to (4), $Y_2$ does not represent one of the formula (19) to (21).

According to the above disclosure, the photosensitizer dye of the present invention contains the above special groups ($X_1$, $X_2$, $Z_1$ and $Z_2$). The photosensitizer dye of the invention has a desirable light absorption capability. In other words, the absorption spectrum of the photosensitizer dye of the present invention is close to the solar light spectrum. Moreover, the absorption coefficient of the photosensitizer dye of the present invention is higher, which suggest that the dye-sensitized solar cell using the photosensitizer dye of the present invention can effectively absorb solar light and convert it into an output current. In the following disclosure, some of the physical properties of the photosensitizer dye of the present invention are introduced.

Reference now is made to the accompanying drawings to describe the specific embodiments and examples of the photosensitizer dye of the present invention.

BRIEF DESCRIPTION OF THE DRAWINGS

The accompanying drawings are included to provide a further understanding of the invention, and are incorporated in and constitute a part of this specification. The drawings illustrate embodiments of the invention and, together with the description, serve to explain the principles of the invention.

DESCRIPTION OF THE PREFERRED EMBODIMENTS

Figure 1:
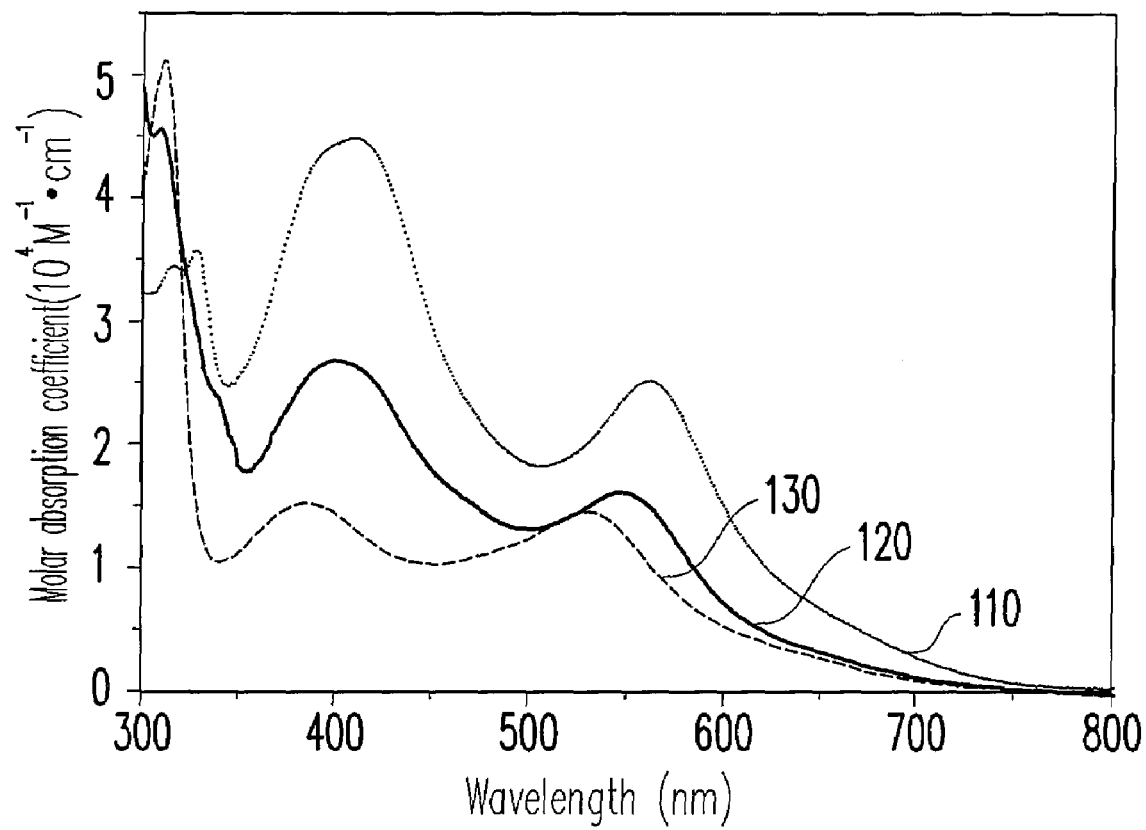
FIG. 1 presents the absorption spectra of the photosensitizer dyes of the present invention (CYC-B5 and CYC-B6S) and a conventional photosensitizer dye (N3).

The present invention provides a photosensitizer dye, wherein the photosensitizer dyes is a ruthenium (Ru) complex represented by the following general formula (1):

Formula (1)

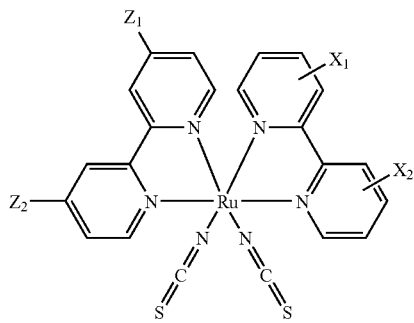

wherein $X_1$ represents one of the following formulas (2) to (18), and $X_2$ represents hydrogen (H) or both $X_2$ and $X_1$ represent one of the following formulas (2) to (18).

(7)

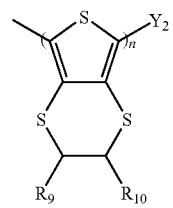

(8)

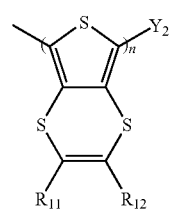

(9)

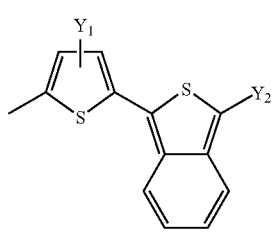

(10)

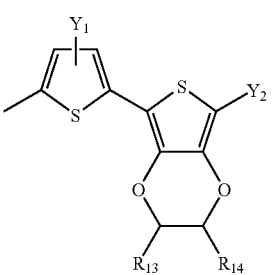

-continued
(11)
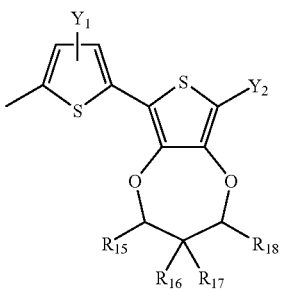
(12)
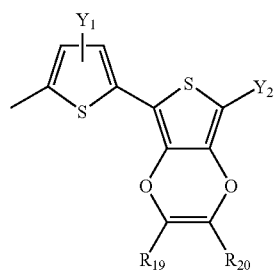
(13)
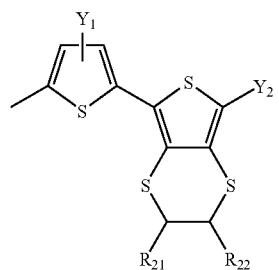
(14)
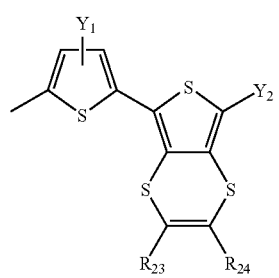
(15)
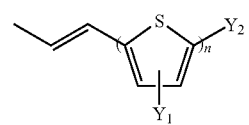
(16)
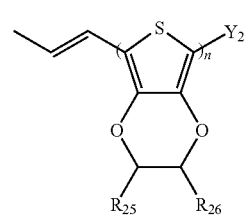
-continued
(17)
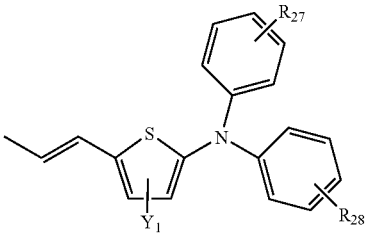
(18)
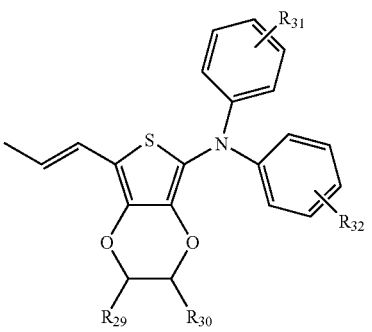
wherein $R_1, R_2, R_3, R_4, R_5, R_6, R_7, R_8, R_9, R_{10}, R_{11}, R_{12}, R_{13}, R_{14}, R_{15}, R_{16}, R_{17}, R_{18}, R_{19}, R_{20}, R_{21}, R_{22}, R_{23}, R_{24}, R_{25}, R_{26}, R_{27}, R_{28}, R_{29}, R30, R_{31}$ and $R_{32}$ independently represents one of H, $C_mH_{2m+1}$ (m=1 to 15), $OC_pH_{2p+1}$ (p=1 to 15), and n=1 to 4, and wherein $Y_1$ and $Y_2$ independently represent one of formulas (19) to (34).
(19) H
(20) $C_iH_{2i+1}$
(21) $OC_jH_{2j+1}$
(22) $SC_kH_{2k+1}$
(23)
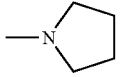
(24)
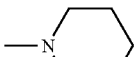
(25)
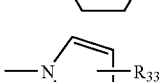
(26)
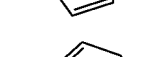
(27)
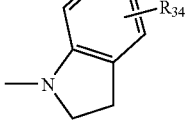
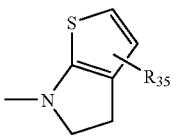

-continued

(28) 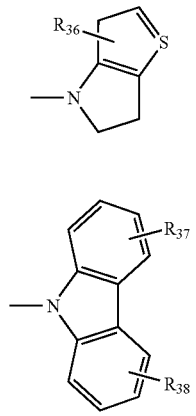

(29) 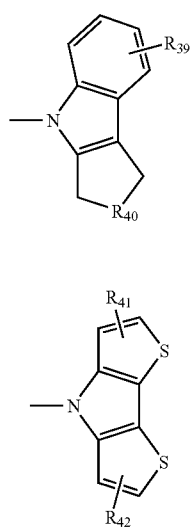

(30)

(31)

(32) 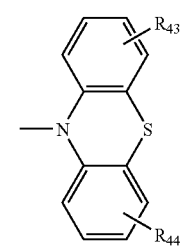

(33) 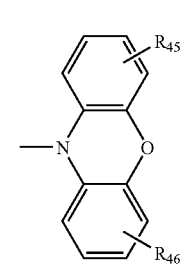

-continued

(34) 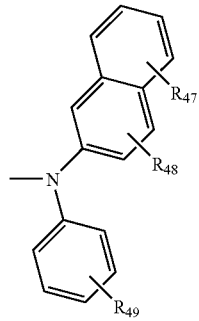

wherein $Z_1$ represents one of following formulas (35) to (41), and $Z_2$ represents hydrogen or one of the formulas (35) to (41) or a group the same as $Z_1$, $$—COOA_1 \quad (35)$$

$$—PO_3HA_1 \quad (36)$$

(37)

(38)

(39)

(40)

(41)

wherein $A_1$ represents hydrogen (H), lithium (Li), sodium (Na), potassium K or tetra-alkyl ammonium groups as in the following general formula (42),

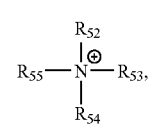 (42)

wherein $R_{52}$, $R_{53}$, $R_{54}$ and $R_{55}$ independently represents H or $C_mH_{2m+1}$ (m=1 to 15).

When $Z_1$ and $Z_2$ both represent formula (35) and $X_1$ represents one of the formulas (2) to (4) and $X_2$ represents hydrogen, $Y_2$ does not represent one of formulas (19) to (21).

More particularly, when $Z_1$ and $Z_2$ both represent formula (35) and $X_1$ represents formula (2) and $X_2$ represents hydrogen, the photosensitizer dye of the invention is represented by the following general formula (43), wherein $Y_2$ does not represent formula (19), (20 or (21). In other words, $Y_2$ represents one of formulas (22) to (34).

Formula (43)

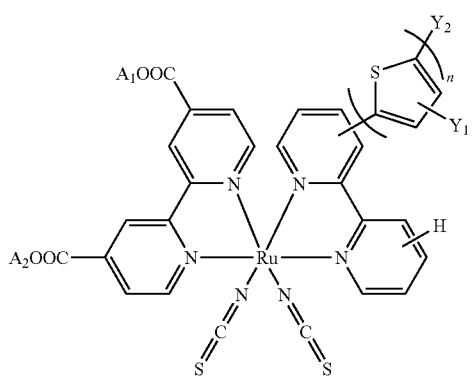

(43)

When $Z_1$ and $Z_2$ both represent formula (35) while $X_1$ represents formula (3) and $X_2$ represents hydrogen, the photosensitizer dye of the present invention is represented the general formula (44), wherein $Y_2$ does not represent formula (19), (20) or (21). In other words, $Y_2$ represents one of formulas (22) to (34).

Formula (44)

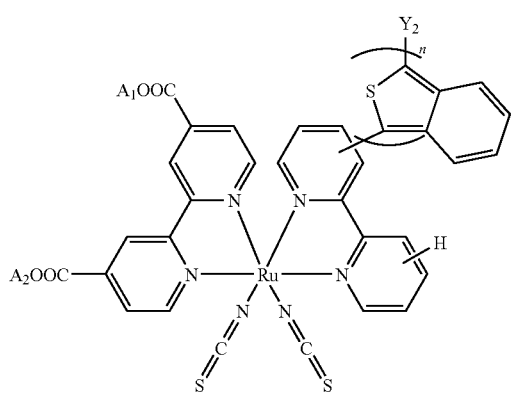

(44)

When $Z_1$ and $Z_2$ both represent formula (35), $X_1$ represents formula (4) and $X_2$ represents hydrogen, the photosensitizer dye of the present invention is represented the general formula (45), wherein $Y_2$ does not represent formula (19), (20) or (21). In other words, $Y_2$ represents one of the formulas (22) to (34). Moreover $R_1$ and $R_2$ are both hydrogen.

Formula (45)

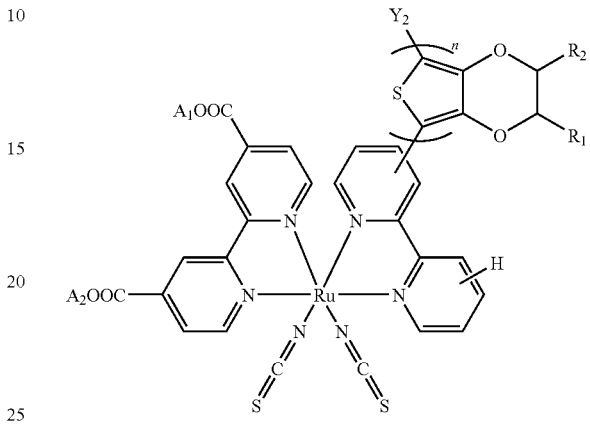

(45)

When $Z_1$ and $Z_2$ both represent formula (35) and $X_1$ and $X_2$ both represent one of the formulas (2) to (4), $Y_2$ does not represent one of the formulas (19) to (21).

More particularly, when $Z_1$ and $Z_2$ both represent formula (35) and $X_1$ and $X_2$ both represent one of the formulas (2), the photosensitizer dye of the invention is represented by the following general formula (46), wherein $Y_2$ does not represent formula (19), (20) or (21). In other words, $Y_2$ represents one of the formulas (22) to (34).

Formula (46)

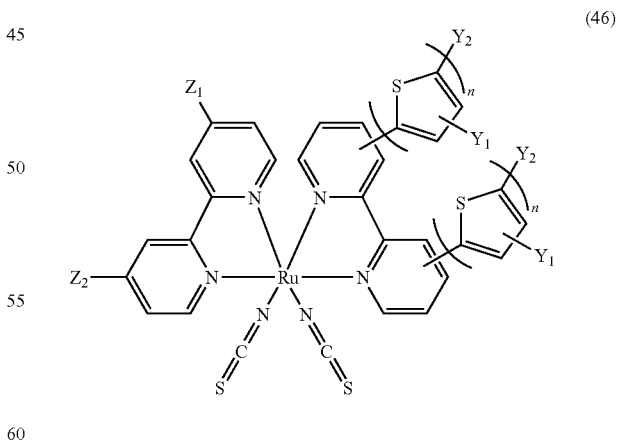

(46)

When $Z_1$ and $Z_2$ both represent formula (35) and both $X_1$ and $X_2$ represent formula (3), the photosensitizer dye of the present invention is represented the general formula (47), wherein $Y_2$ does not represent formula (19), (20) or (21). In other words, $Y_2$ represents one of formulas (22) to (34).

Formula (47)

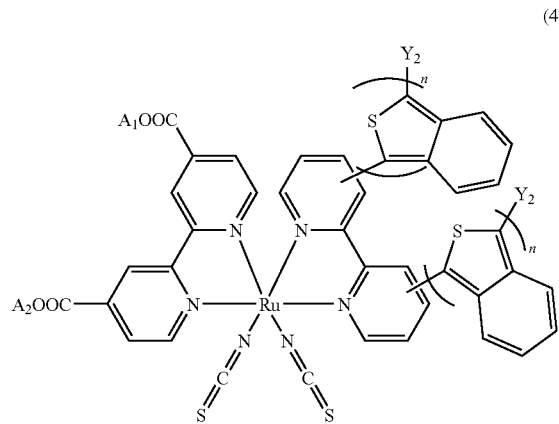

(47)

When $Z_1$ and $Z_2$ both represent formula (35) while both $X_1$ and $X_2$ represent formula (4), the photosensitizer dye of the present invention is represented the general formula (48), wherein $Y_2$ does not represent formula (19), (20) or (21). In other words, $Y_2$ represents one of formulas (22)~(34) and both $R_1$ and $R_2$ are hydrogen.

Formula (48)

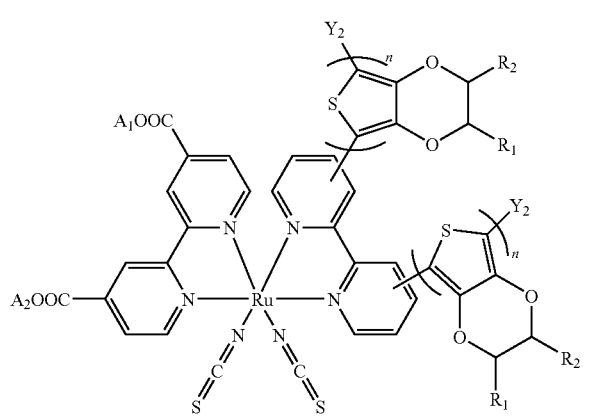

(48)

According to the present invention, the photosensitizer dye contains the above functional groups ($X_1$, $X_2$, $Z_1$ and $Z_2$). Hence, the photosensitizer dye is provided with a desirable light absorption capability. In other words, the absorption spectrum of the photosensitizer dye of the present invention is close to the solar light spectrum, and the absorption coefficient of the photosensitizer dye of the present invention is higher. Ultimately, a dye-sensitized solar cell using the photosensitizer dye of the present invention can effectively absorb solar light and convert it into an output current. In the following disclosure, some of the physical properties of the photosensitizer dye of the present invention will be introduced.

Moreover, the potential energy level of the excitation state of the photosensitizer dye has to be compatible with the potential energy level of the conductive band of the metal oxide (for example, titanium dioxide or zinc oxide, etc.) used in the dye-sensitized solar cells. Accordingly, electrons can be effectively transported (from the photosensitizer dye to the metal oxide), and energy loss during the conduction process is minimized.

Additionally, the oxidation potential (potential energy level of the highest occupied molecular orbital (HOMO)) of the photosensitizer dye has to be slightly lower than that of the electrolytes (such as, iodine ions) or other materials having hole conduction property. Accordingly, the photosensitizer dye, after losing an electron, can effectively retrieve an electron from the electrolytes or other hole-conduction materials to restore to the original state.

Since the photosensitizer dye contains the above special groups ($X_1$, $X_2$, $Z_1$ and $Z_2$), the potential energy structure of the photosensitizer dye is compatible well with the oxidation potential of the cathode of a typical dye-sensitized solar cell (DSCs) and the energy gap of the conductive band of the anode. As a result, the resulting dye-sensitized solar cell (DSSC) has high photoelectric conversion efficiency.

The following embodiments describe the synthesis of a ruthenium (Ru) complex photosensitizer dye of the present invention. It should be appreciated that the following description should be regarded as illustrative rather than restrictive.

FIRST SYNTHESIS EXAMPLE

The chemical compound (represented as CYC-B5) is used as an example to illustrate the synthesis of a ruthenium (Ru) complex photosensitizer dye of the first synthesis example of the present invention.

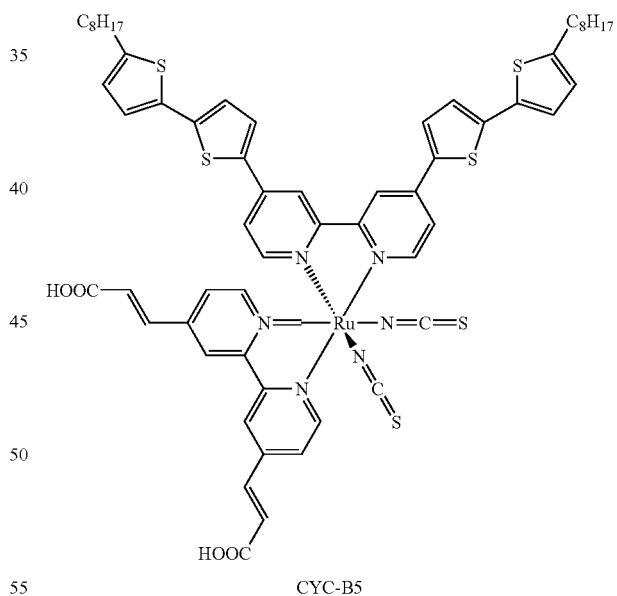

CYC-B5

CYC-B5 is a compound with a structure of formula (1) when $X_1$ and $X_2$ in formula (1) are the same group and $X_1$ represents the above formula (2), $Y_1$ in formula (2) represents formula (19), $Y_2$ represents formula (20), $C_iH_{2i+1}$ in formula (20) is $C_8H_{17}$, and n=2. Wherein $Z_1$ and $Z_2$ are the same group and $Z_1$ represents the group of formula (37), and $A_1$ represents hydrogen (H).

The process flow in synthesizing a first ligand (Ligand-1), which is 4,4'-bis (5-octyl-2.2'-bithiophen-5-yl)-2,2'-bipyridine, of CYC-B5 is presented as follows.

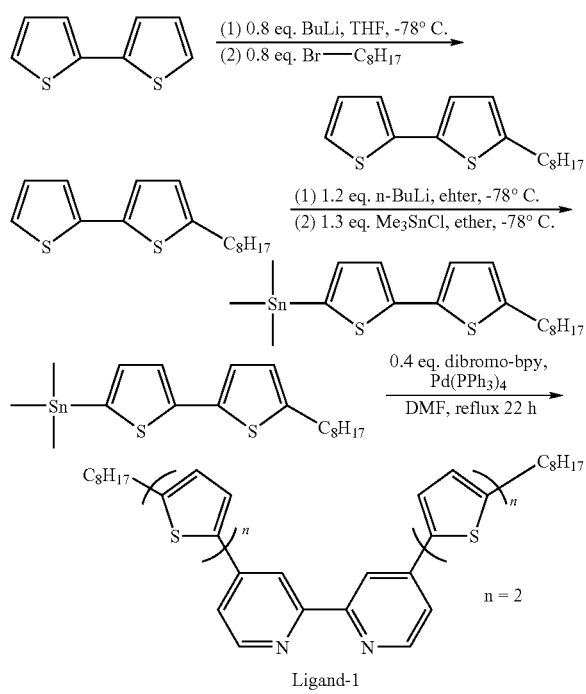

Ligand-1 wherein THF represents tetrahydrofuran ($C_4H_8O$), DMF represents dimethylformamide ($C_3H_7NO$), and ether is ethyl ether ($C_4H_{10}O$).

The process is commenced by placing about 4 g of bithiophene in a round bottom flask, followed by adding an anhydrous tetrahydrofuran solvent to dissolve the bithiophene. The temperature of the resulting solution is then lowered to −78° C. (for example, using liquid nitrogen plus ethanol as a cryogen). Thereafter, about 7.6 ml of n-butyl lithium (n-BuLi) (2.5 M, dissolved in hexane) is gradually drop-added into the bithiophene solution. After the temperature of the resulting solution has returned to room temperature, the solution is continuously stirred for about 15 minutes.

The process is then continued by adding 4.6 ml of 1-bromooctane (Br—$C_8H_{17}$) to the solution, and the solution is continuously stirred for about 10 hours. After a predetermined period of reaction time, deionized water is added to terminate the reaction, and an extraction is performed by adding ether to the solution. An organic layer is collected, and another extraction of the organic layer is performed by using respectively a saturated sodium hydrogen carbonate aqueous solution, deionized water and a saturated sodium chloride solution. The resulting crude product is purified using column chromatography (eluent being hexane) to obtain 5.4 gm of an intermediate product. The intermediate product is 4,4'-bis(5-octyl-2.2'-bithiophene, $C_{16}H_{22}S_2$), which is represented by formula (49), with a yield of about 80.5%.

Thereafter, about 4.2 g of 5-octyl-2.2'-bithiophene is dissolved in an anhydrous THF. The temperature of the solution is lowered to −78° C. using a cryogen, followed by gradually drop-adding 6.0 ml of n-BuLi (2.5M, dissolved in hexane) to the solution. After this, the temperature of the solution is returned to room temperature, and the solution is stirred for about two hours. Then, the temperature of the solution is again lowered to −78° C., and about 3.16 g of chlorotrimethyl stannane ($C_3H_9ClSn$) (dissolved in an appropriate amount of THF) is added to the solution.

After the temperature of the solution is returned to room temperature, the solution is continuously stirred for about 12 hours. Thereafter, deionized water is added to terminate the reaction, and an extraction is performed using respectively a saturated sodium hydrogen carbonate aqueous solution, deionized water and a saturated sodium chloride solution. An organic layer is then collected, and the solvent is removed to obtain about 6.0 g of the crude product, which is trimethyl 5-octyl-2.2'-bithiophene)stannane, ($C_{19}H_{30}S_2Sn$).

Thereafter, about 6.0 g of 8-(trimethyltin)-2-octyl-bithiophene and about 2.0 g of 4-4'-dibromo-2,2'-bipyridine (the method of synthesis can be referred to I. Murase, Nippon Kagaku Zasshi, 1956, 77, 682; G. Mnerker and F. H. Case, J. Am. Chem. Soc., 1958, 80, 2745; and D. Wenkert and R. B. Woodward, J. Org. Chem., 1983, 48, 283) are dissolved in 60 ml of anhydrous dimethylformamide (DMF). About 0.44 g of tetrakis(triphenylphosphine)palladium is added as a catalyst. After this, the solution is heated and refluxed for about 22 hours. When the temperature of the solution returns to room temperature, about 5 wt % of ammonium chloride aqueous solution is added to terminate the reaction.

After this, an extraction is performed using dichloromethane, and an organic layer is collected. Another extraction of the organic layer is conducted using respectively a sodium hydrogen carbonate aqueous solution, deionized water and a saturated sodium chloride aqueous solution. After removing the solvent of the organic layer, a crude product is obtained. The crude product is purified by column chromatography (using hexane as an eluent), and the remaining solid substance is further extracted with a Soxhlet extractor using ethyl acetate to obtain 1.0 of the first ligand (represented as Ligand-1) with a yield of about 9.4%.

The process flow in synthesizing a photosensitizer dye (CYC-B5) containing ruthenium (Ru)-complex is as follows.

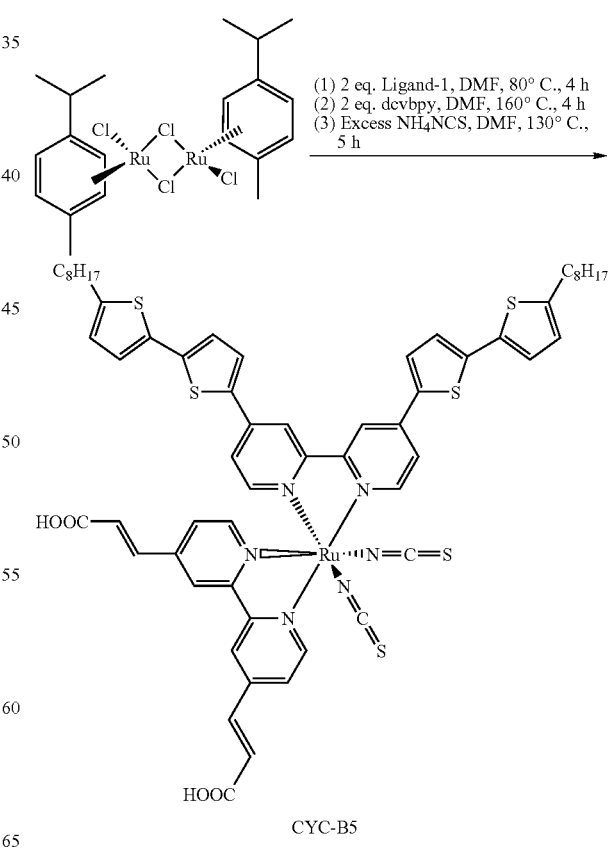

CYC-B5

After the preparation of Ligand-1, 0.4323 g of [RuCl$_2$(p-cymene)]$_2$ and 1.0 g of Ligand-1 are dissolved in 30 ml of the anhydrous DMF. The solution is then heated to about 80° C. for about 4 hours. After this, about 0.4183 g of 4,4'-bis (E-carboxyvinyl)-2,2'-bi-pyridine (dcvbpy) (the method of synthesis can be referred to Klein et al., Inorg. Chem., 2005, 44, 178) is added to the solution, followed by heating the solution to about 160° C. for 4 hours. It is worthy to note that the above reaction must be conducted in the dark to prevent the generation of isomers due to light.

Then, an excessive amount of NH$_4$NCS is added to the solution, and the reaction is allowed to continue for about 5 hours at a temperature about 130° C. After the reaction is completed, the temperature of the solution is returned to room temperature. The solution is concentrated by removing the solvent DMF using a vacuum system, followed by a washing process using respectively deionized water, sodium hydroxide solution at pH 12 and ethyl ether to obtain a solid substance. A crude product is ultimately obtained after vacuum filtration.

After dissolving the crude product in methanol and passing the solution through a column (using methanol as an eluent), a dark color portion is collected and methanol is removed by rotary evaporation. The resulting black solid substance is placed in a Soxhlet extractor to be further purified. The purification process is described as follows. Using ethyl acetate as a solvent to remove impurities that are dissolvable in ethyl acetate. Then, acetone is used as a solvent to remove impurities that are dissolvable in acetone. The black solid substance, after being sequentially washed with ethyl acetate and acetone, is dissolved in a mixture solution of methanol and tetra-butyl ammonium hydroxide aqueous solution. The resulting liquid then passes through a column (Sephadex LH-20), and a darker color portion of the liquid is collected. Few drops of a 0.01M nitric acid aqueous solution are added to the liquid containing the product for adjusting the pH to 3, and a precipitation of about 0.69 g is obtained. The precipitation is the product (CYC-B5). The yield of CYC-B5 is about 40.0%.

Structural analysis and evaluation of the product (CYC-B5) are discussed as follows.

Mass spectrometry analysis theoretical value: m/z −1222.2 ([M+]); Mass spectrometry analysis (LRMS (FAB)) experimental value: m/z −1222.2 (m) ([M+]). Mass spectrometry analysis (HRMS (FAB)) experimental value: m/z −1222.2004. CYC-B5 (C$_{60}$H$_{60}$N$_6$O$_4$S$_6$Ru) elemental analysis theoretical value: C, 58.94; H, 4.95; N, 6.87%. Elemental analysis experimental values: C, 58.82; H, 5.79. N, 6.43%. $^1$H-NMR spectrum signal (500 MHz, $_H$/ppm in d$_6$-DMSO, J Hz): 9.26 (H); 9.15 (2 protons); 9.05 (H); 8.99 (H); 8.91 (H); 8.22 (2 protons); 8.15 (H); 8.02 (H); 7.80 (H); 7.73 (H); 7.55 (H); 7.51 (H); 7.48 (2 protons); 7.39 (2 protons); 7.34 (H); 7.25 (H); 7.21 (H); 6.98 (H); 6.90 (H); 6.84 (H); 2.81 (2H); 2.78 (2H); 1.65 (2H); 1.62 (2H); 1.26 (20H); 0.85 (6H).

SECOND SYNTHESIS EXAMPLE

The second synthesis example is used to illustrate the synthesis of a chemical compound according to another embodiment of invention. This chemical compound is represented as CYC-B6S.

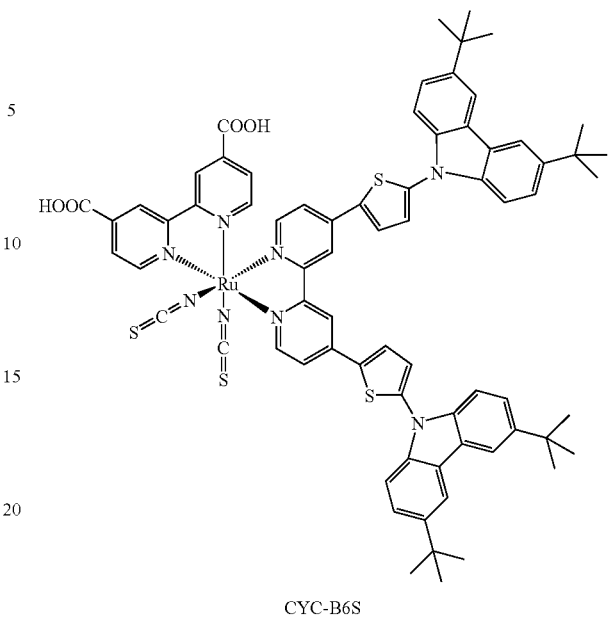

CYC-B6S

CYC-B6S is a compound with a structure of formula (1) when X$_1$ and X$_2$ in formula (1) are the same group, and X$_1$ represents the group of formula (2), and Y$_1$ of formula (2) represents formula (19), Y$_2$ represents formula (29). R$_{37}$ and R$_{38}$ in formula (29) both represent C$_4$H$_9$, and n=1. Wherein Z$_1$ and Z$_2$ are the same group, and Z$_1$ represents the group of formula (35), and A$_1$ represents hydrogen (H).

The process flow in synthesizing a first ligand (represented as Ligand-6S) of CYC-B6S is presented as in the followings.

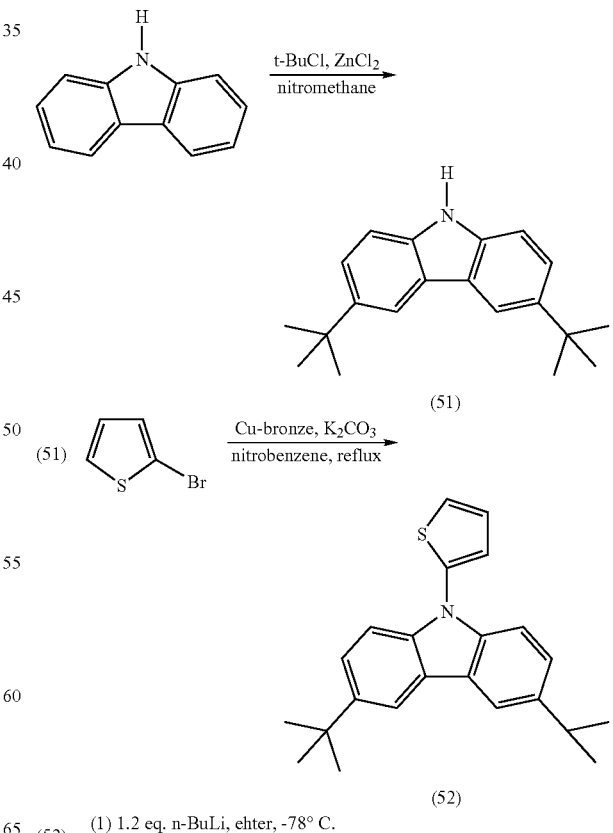

-continued

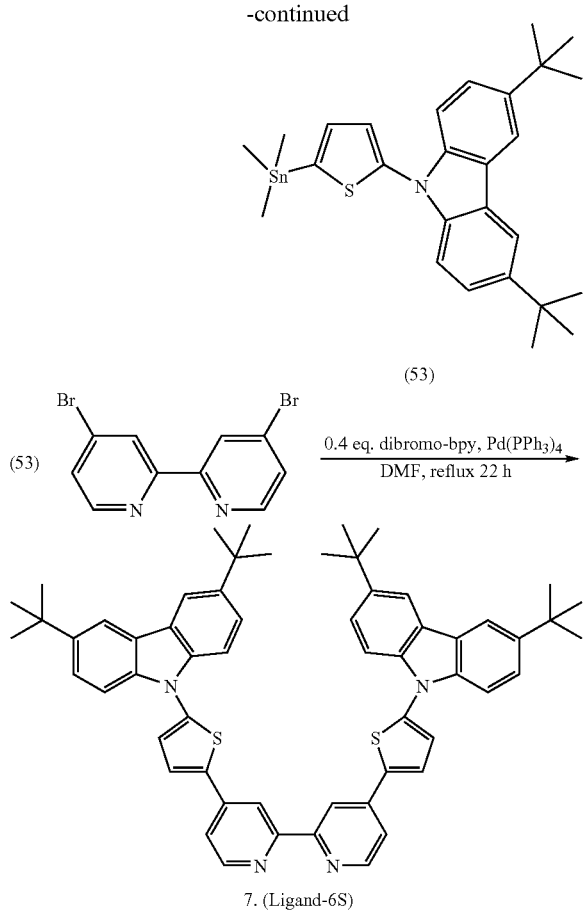

7. (Ligand-6S)

wherein nitromethane represents $CH_3NO_2$, nitrobenzene represents $C_6H_5NO_2$, THF represents tetrahydrofuran, DMF represents dimethylformamide, ether represents ethyl ether.

The process is commenced by placing about 10 g of carbazole ($C_{12}H_9N$) in a round bottom flask, followed by adding 300 ml of nitromethane and 25 gm of ZnCl. Then, 20 ml of tert-butyl chloride (t-BuCl) is gradually drop-added to the solution and the solution is continuously stirred at room temperature for about 20 hours. The resulting solution is transferred to a beaker, and 350 ml of water is added to the beaker for performing a hydrolysis reaction.

After a predetermined period of reaction time, dichloromethane ($CH_2Cl_2$) is added to perform an extraction, and an organic layer is collected. Another extraction of the organic layer is further performed using respectively deionized water and a saturated sodium chloride aqueous solution. The resulting crude product is purified using a recrystallization method (the solvent being hexane) to obtain a first intermediate product (represented by formula (51)), 3,6-di-tert-butylcarbazole, in which the yield is about 60.6%.

About 10.13 gm of the first intermediate product (represented by formula (51)), 6.6 g of potassium carbonate ($K_2CO_3$), 6.7 gm of Cu-bronze and 7.1 g of 2-bromo-thiopene ($C_4H_3B_4S$) are placed in a round bottom flask. Nitrobenzene ($C_6H_5NO_2$) is further added to the flask and a reflux reaction is conducted under nitrogen gas for 80 hours. Thereafter, the solvent is removed, and ammonia is added. The resulting solution is continuously stirred for about 2 hours. A large amount of water and $CHCl_3$ are added to perform an extraction, and an organic layer is collected. Then, the water in the organic layer is removed using magnesium sulfate ($MgSO_4$), and a majority of the solvent is removed after filtering and rotary evaporation. After this, further purification is performed using column chromatography to obtain a second intermediate product (represented by formula (52)), wherein the yield of the second intermediate product is about 57.2%.

Then, 1.48 gm of the second intermediate product is placed in a round bottom beaker with a side arm. Approximately 60 ml of tetrahydrofuran is added to the beaker. The temperature of the round bottom beaker is controlled at about −78° C. (may use ethanol and liquid nitrogen to control the temperature). After this, 2.0 ml of n-butyl lithium (n-BuLi) solution (2.5 M, dissolved in hexane) is slowly injected into the beaker. After the temperature of the solution has returned to room temperature, the solution is stirred for 2 hours. Then, 1.1 g of $Me_3SnCl$ is slowly injected into the solution. After the temperature of the solution has returned to room temperature, the solution is stirred for another 10 hours. A large amount of water and dichloromethane ($CH_2Cl_2$) are added (to dissolve the organic layer) to perform an extraction. After an organic layer (lower layer) is collected, the organic layer is readily washed with saturated NaCl (aq). The solvent in the collected product is removed using rotary evaporation to obtain 2.1 g of the third intermediate product (represented by formula (53)).

About 2.1 g of the third intermediate product and 2.0 g of 4,4'-dibromo-2,2'-biphyridine (the method of synthesis can be referred to I. Murase, Nippon Kagaku Zasshi, 1956, 77, 682; G. Mnerker and F. H. Case, J. Am. Chem. Soc., 1958, 80, 2745; and D. Wenkert and R. B. Woodward, J. Org. Chem., 1983, 48, 283) are dissolved in 60 ml of anhydrous dimethylformamide (DMF), and about 0.25 g of tetrakis(triphenylphosphine)palladium is added as a catalyst. The reactants are heated and refluxed for about 22 hours. When the temperature of the reactants returns to room temperature, about 5 wt % of ammonium chloride aqueous solution is added to to terminate the reaction. An extraction is performed using dichloromethane, and an organic layer is collected.

Thereafter, another extraction of the organic layer is conducted using respectively a sodium hydrogen carbonate aqueous solution, deionized water and a saturated sodium chloride aqueous solution. When the solvent of the organic layer is removed, a crude product is obtained. The crude product is further purified by a Soxhlet extractor (eluent being ethyl acetate) to obtain 1.1 g of product, which is Ligand-6S, and the yield of is Ligand-6S is about 71.1%.

The process flow in synthesizing a photosensitizer dye containing ruthenium (Ru)-complex (CYC-B6S) is as follows:

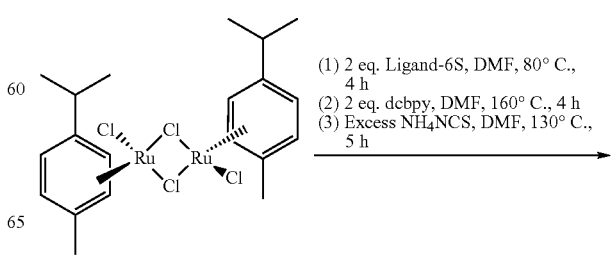

(1) 2 eq. Ligand-6S, DMF, 80° C., 4 h
(2) 2 eq. dcbpy, DMF, 160° C., 4 h
(3) Excess NH$_4$NCS, DMF, 130° C., 5 h -continued

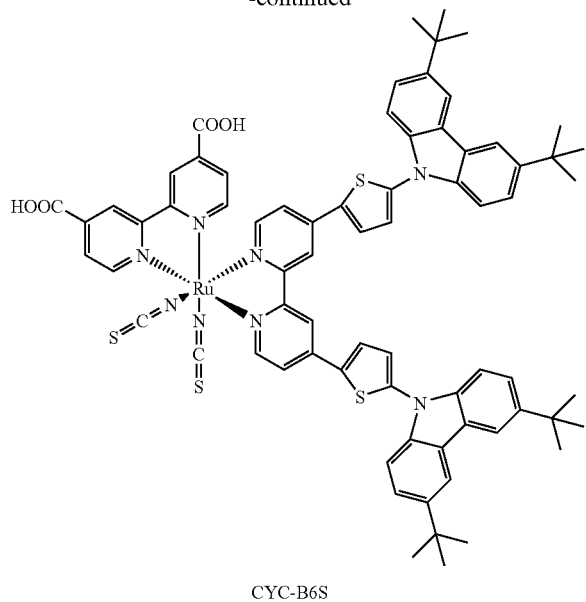

CYC-B6S wherein DMF represents dimethylformamide.

After the preparation of Ligand-6S, 0.3848 gm of [RuCl$_2$(p-cymene)]$_2$ and 1.1 gm of Ligand-6S are dissolved in 80 ml of anhydrous dimethylformamide, and the resulting solution is heated to 80° C. After allowing the reaction to continue for 4 hours, 0.31 gm of dcbpy (4,4'-dicarboxylic acid-2,2'-bipyridine) is added. The solution is heated to 160° C. and the reaction is continued for another 4 hours. It is worthy to note that the above chemical reactions must be conducted in the dark to prevent the generation of isomers due to light. Thereafter, an excessive amount of NH$_4$NCS is added to the solution, and the reaction is continued for about 5 hours at a temperature about 130° C. Subsequent to the completion of the reaction, the temperature of the solution is returned to room temperature and then the solution is concentrated by removing some of the solvent DMF using a vacuum system. Deionized water, sodium hydroxide solution at pH 12 and ether respectively are respectively used to wash the solid substance, followed by vacuum filtration to obtain a crude product. The crude product is then dissolved in methanol. After passing the solution through a column (the eluent being methanol), a dark color portion of the solution is collected and methanol is removed by rotary evaporation.

Thereafter, the resulting black solid substance is placed in a Soxhlet extractor to be further purified. The purification process includes using ethyl acetate as a solvent to remove impurities that are dissolvable in ethyl acetate. Then, acetone is used as a solvent to remove impurities that are dissolvable in acetone. The black solid substance, after being sequentially washed with ethyl acetate and acetone, is dissolved in a mixture solution of methanol and tetra-butyl ammonium hydroxide aqueous solution. The resulting liquid then passes through a column (Sephadex LH-20), and a darker color portion of the liquid is collected. Few drops of a 0.01M nitric acid aqueous solution are added to adjust the pH of the liquid containing the product to 3, and a precipitation is resulted. The precipitation is the product (CYC-B6S) of about 0.69 g in weight, and the yield of CYC-B6S is about 40.3%.

Structural Analysis and Evaluation of Product (CYC-B6S)

Mass spectrometry analysis theoretical value: m/z −1336.3 ([M+]); Mass spectrometry analysis (LRMS (FAB)) experimental value: m/z −1336.0 (m) ([M]+). Mass spectrometry analysis (HRMS (FAB)) experimental value: m/z −1336.3160. CYC-B6S (C$_{72}$H$_{66}$N$_8$O$_4$S$_4$Ru) elemental analysis theoretical value: C, 64.15; H, 6.10; N, 7.83%. $^1$H-NMR spectrum signal (500 MHz, H/ppm in d6-DMSO, J Hz): 9.45 (H); 9.25 (H); 9.17 (H); 9.13 (H); 9.01 (H); 8.97 (H); 8.34~8.29 (6 protons); 8.19 (H); 7.95 (H); 7.67 (2H); 7.62~7.57 (4 protons); 7.$_{.55}$ (H); 7.50 (6 protons); 1.43 (18H); 1.39 (18H).

The method in measuring the absorption coefficient of the photosensitizer dye of the present invention, and comparisons between the absorption coefficients of CYC-B5 and CYC-B6S, and the positions of the absorption peaks of the longest wavelengths and the absorption coefficients of those wavelengths of different conventional photosensitizer dyes are presented. The method in measuring the absorption coefficient of a photosensitizer dye of the present invention includes providing a photosensitizer dye solution of a known concentration and then placing an appropriate amount of the solution in a quartz sample cell. The sample cell is further placed in a UV/Vis Spectrophotometer for analysis. The absorption coefficient can be calculated by using the Beer's law (A=εbc, A:absorbance; ε: absorption coefficient; b: beam path; c: concentration of the sample). The absorption coefficients of the photosensitizer dyes of the present invention (CYC-B5 and CYC-B6S) are compared with the absorption coefficients of various conventional photosensitizer dyes, and the results are summarized in Table 1.

The conventional photosensitizer dye, "N3", listed in Table 1, is disclosed in M. Grätzel, *J. Photochem. A*, 2004, 164, 3 and M. K. Nazeeruddin et al., *J. Am. Chem. Soc.* 1993, 115, 6382; the conventional photosensitizer dye, "Black dye", listed in Table 1, is disclosed in M. K. Nazeeruddin et al., *J. Am. Chem. Soc.*, 2001, 123, 1613; the conventional photosensitizer dye, "Z-910", listed in Table 1, is disclosed in P. Wang, et al., *Adv. Mater.* 2004, 16, 1806.

TABLE 1

| Photosensitizer Dye | Position of the absorption peak of the longest wavelength (nm) | Absorption coefficient of the absorption peak of the longest wavelength (M$^{-1}$ cm$^{-1}$) |
| --- | --- | --- |
| CYC-B5 | 562 | 25100 |
| CYC-B6S | 548 | 16100 |
| N3 | 530 | 14500 |
| Black dye | 600 | 7640 |
| Z910 | 543 | 16850 |

Based on the results reviewed in Table 1, the absorption coefficient of the photosensitizer dye CYC-B5 is higher and the absorption wavelength of the photosensitizer dye CYC-B5 is longer than those of the conventional photosensitizer dyes. The absorption coefficient of the photosensitizer dye CYC-B6S is near to those of the conventional dyes, and the absorption wavelength of the photosensitizer dye CYC-B5 is longer. Since the photosensitizer dye of the present invention contains the above-mentioned special groups (X$_1$, X$_2$, Z$_1$ and Z$_2$), the photosensitizer dye has a desirable light absorption capability. In other words, a dye-sensitized solar cell using the photosensitizer dye of the present invention can effectively absorb solar light and convert the solar light into an output current.

Figure 2:
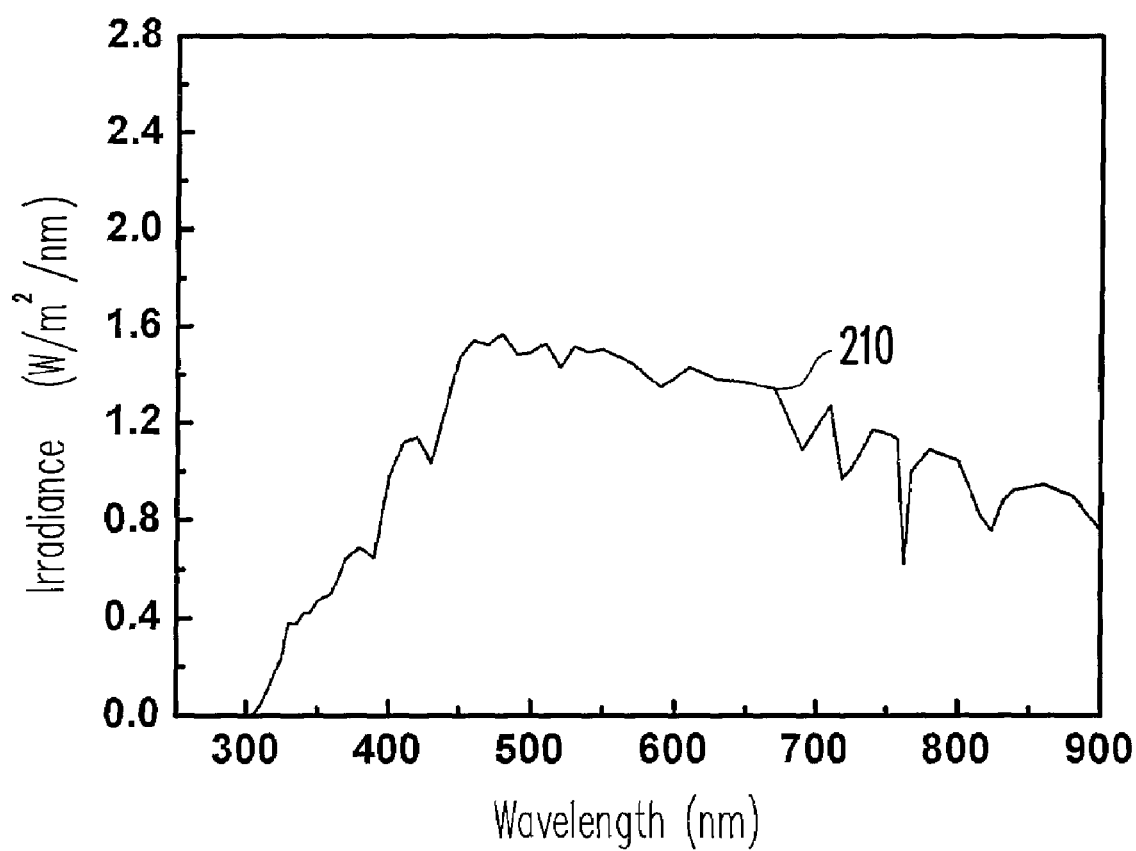
FIG. 2 presents the absorption spectrum of solar light.

Additionally, the above detection method is used to obtain an absorption spectra for CYC-B5, CYC-B6S and N3, as shown in FIG. 1. Referring to FIG. 1, the curve 110 represents the absorption spectrum of CYC-B5, the curve 120 represents the absorption spectrum of CYC-B6S, and the curve 130 represents the absorption spectrum of N3. The curves 110, 120, 130 in FIG. 1 are respectively compared with the solar spectrum (as shown by curve 210 in FIG. 2) disclosed in Annual Book of ASTM Standard, G159-98 Standard tables for references solar spectral irradiance at air mass 1.5: direct normal and hemispherical for a 37° tilted surface, Vol. 14.04 (2003). As shown in FIGS. 1 and 2, curves 110, 120 are closer to the solar spectrum curve 210 than curve 130. In other words, the absorption spectra of CYC-B5 and CYC-B6S are much closer to the solar spectrum than the absorption spectrum of N3. Accordingly, a dye-sensitized solar cell using the photosensitizer dye of the present invention can effectively absorb solar light and convert the solar light into an output current.

Thereafter, the photosensitizer dyes CYC-B5 and CYC-B6S of the present invention are respectively used as a material for a dye layer in a dye-sensitized solar cell and the efficiency of the cell is measured.

The method of forming a dye-sensitized solar cell using respectively CYC-B5 and CYC-B6S as a material of the dye layer is described as follows. A titanium dioxide ($TiO_2$) electrode submerged in a CYC-B5 or CYC-B6S containing solution for a period of time. CYC-B5 or CYC-B6S attaches to the surface of the $TiO_2$ electrode in a self-assembly manner.

The $TiO_2$ electrode is removed from the dye-containing solution, and is further rinsed and dried. The electrode is sealed with epoxy. After filling with an electrolyte solution and sealing the injection opening, the fabrication of a dye-sensitized solar cell is completed. A dye-sensitized solar cell is fabricated using CYC-B5 or CYC-B6S as a material of the dye layer. Then, the dye-sensitized solar cell is irradiated by a virtual sun light with a light source AM1.5G (light intensity of 100 mW/cm$^2$), and the voltage, the current, the photoelectric conversion efficiency of the cell are measured. The results of the measurements are summarized in Table 2. Similarly, the above method is used to fabricate a dye-sensitized solar cell using N3 as a material of the dye layer, and the voltage, the current and the photoelectric conversion efficiency are measured and reported in Table 2.

Figure 3:
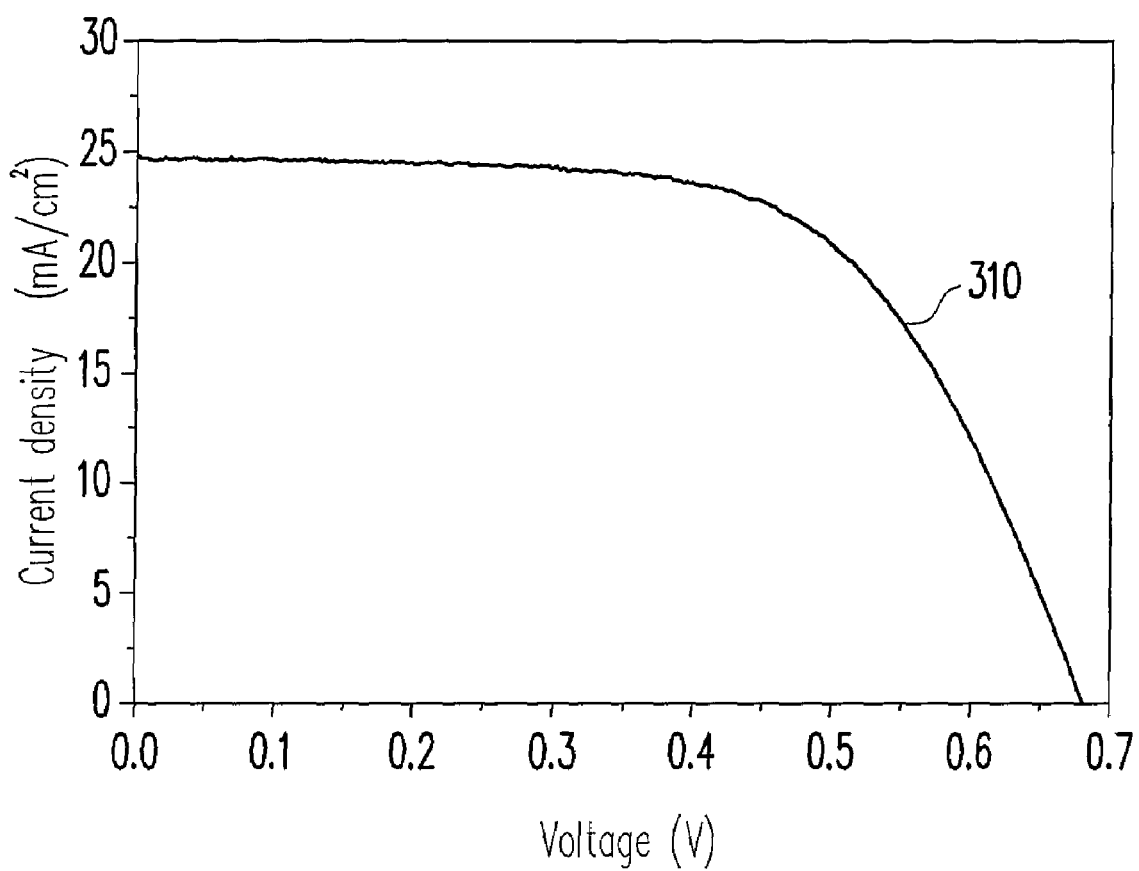
FIG. 3 presents the current-potential curve of a dye-sensitized solar cell fabricated using CYC-B5 as a material for the dye layer.
Figure 4:
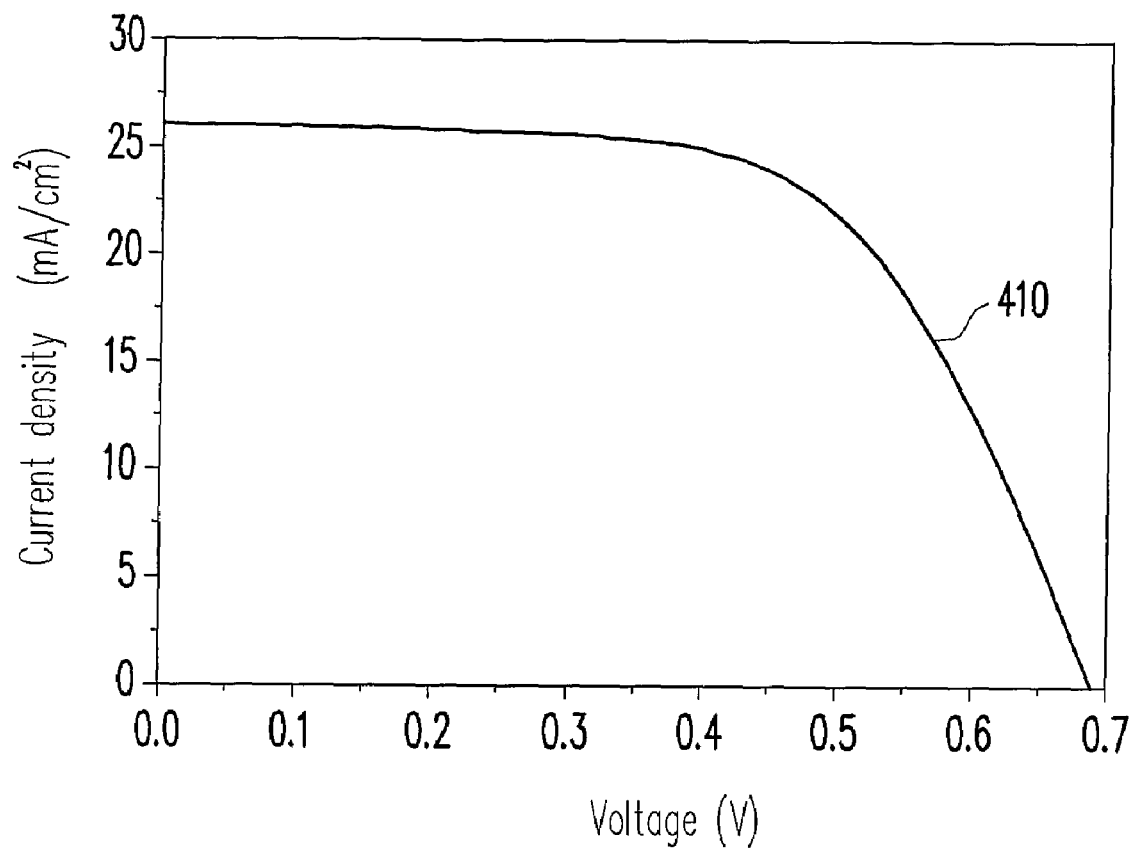
FIG. 4 presents the current-potential curve of a dye-sensitized solar cell fabricated using CYC-B6S as a material for the dye layer.

Moreover, the current density-voltage curve of the dye-sensitized solar cell fabricated using CYC-B5 as a material of the dye layer is presented as curve 310 in FIG. 3. The current density-voltage curve of the dye-sensitized solar cell fabricated using CYC-B6S as a material of the dye layer is presented as curve 410 in FIG. 4.

TABLE 2

| Photosensitizer Dye | Short circuit current density, Jsc (mA/cm$^2$) | Open circuit voltage, Voc (mV) | Fill factor, FF | Photoelectric conversion efficiency, η (%) |
|---|---|---|---|---|
| CYC-B5 | 24.8 | 681 | 0.620 | 10.5 |
| CYC-B6S | 26.1 | 680 | 0.620 | 11.0 |
| N3 | 20.6 | 749 | 0.646 | 9.95 |

Based on the results presented in Table 2, using CYC-B5 or CYC-B6S as a dye to fabricate a dye-sensitized solar cell, the photoelectric conversion efficiency is about 10.5% or 11.0%, whereas the photoelectric conversion efficiency of a dye-sensitized solar cell fabricated using N3 as a dye is only about 9.95%. As confirmed by the results from Table 2, due to the presence of the special groups ($X_1$, $X_2$, $Z_1$, $Z_2$) on the photosensitizer dye of the present invention, the photoelectric conversion efficiency is higher than the dye-sensitized solar cell containing a conventional photosensitizer dye.

Accordingly, due to the presence of the special groups ($X_1$, $X_2$, $Z_1$, $Z_2$) on the photosensitizer dye of the present invention, the absorption spectrum of the photosensitizer dye of the present invention is closer to the solar spectrum and the absorption coefficient of the photosensitizer of the present invention is higher. Moreover, the potential energy structure of the photosensitizer dye of the invention is compatible well with the oxidation potential of the cathode and the energy gap of the conductive band of the anode of a typical dye-sensitized solar cell (DSC). As a result, the resulting dye-sensitized solar cell (DSC) of the invention has higher photoelectric conversion efficiency than a conventional cell.

It will be apparent to those skilled in the art that various modifications and variations can be made to the structure of the present invention without departing from the scope or spirit of the invention. In view of the foregoing descriptions, it is intended that the present invention covers modifications and variations of this invention if they fall within the scope of the following claims and their equivalents.

What is claimed is:

1. A photosensitizer dye, wherein the photosensitizer dye is a ruthenium (Ru) complex represented by the following general formula (1), Formula (1):

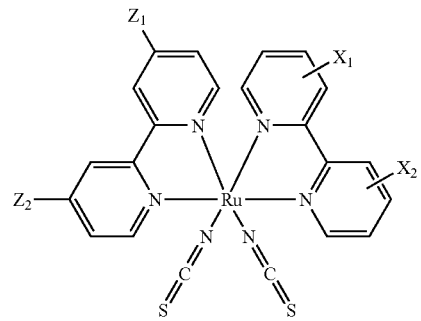

wherein $X_1$ represents one of formula (2) to (14) and (16) to (18) and $X_2$ represents hydrogen atom or $X_1$ and $X_2$ both represent one of the formula (2) to (14) and (16) to (18),

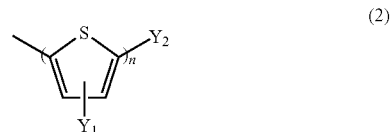

(2)

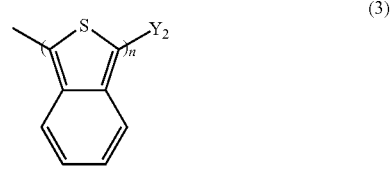

(3)

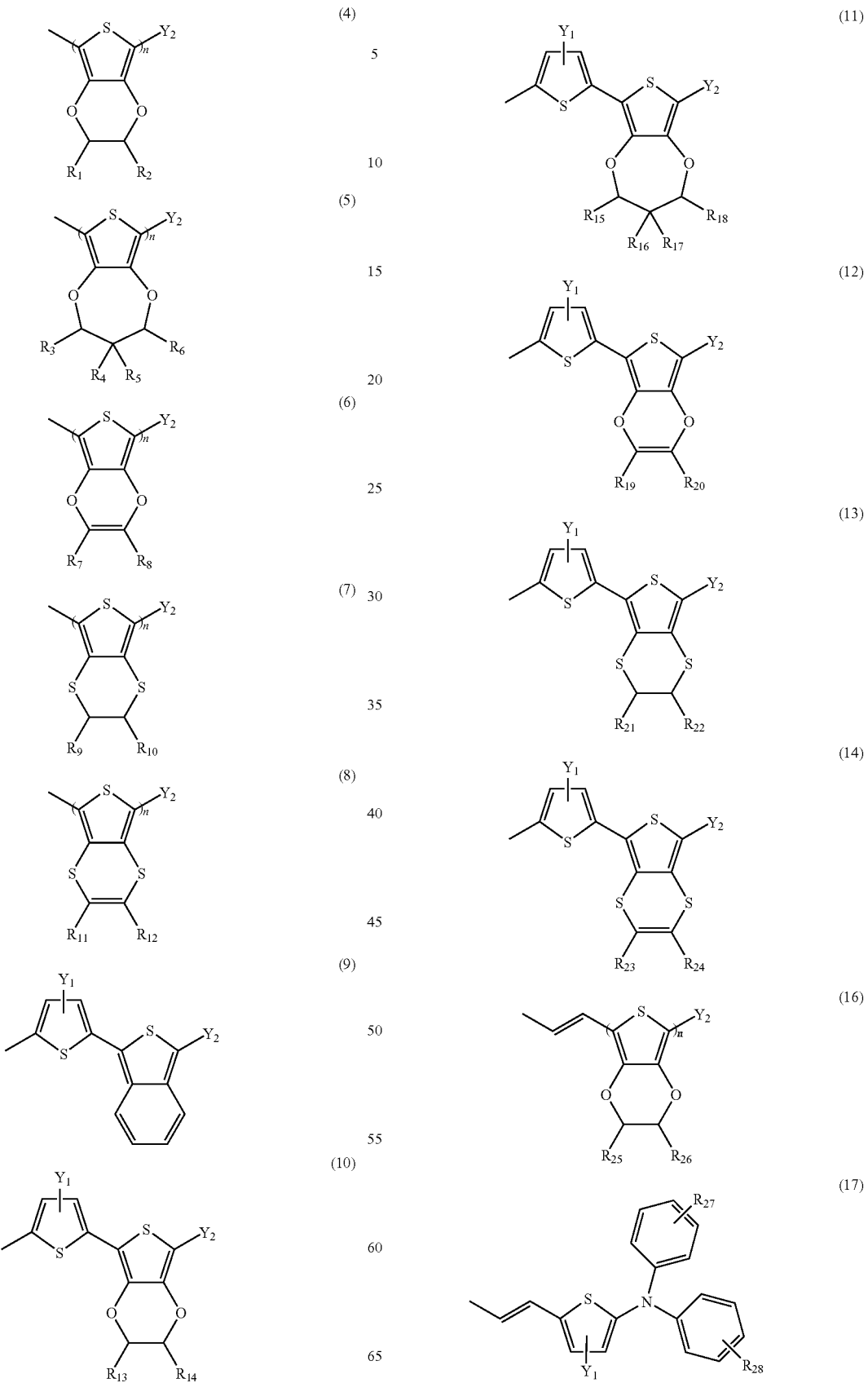

-continued

(18)
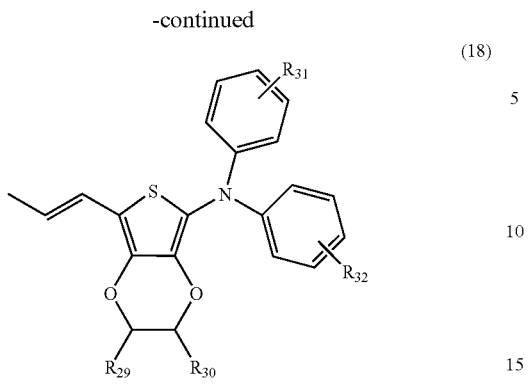

wherein $R_1$, $R_2$, $R_3$, $R_4$, $R_5$, $R_6$, $R_7$, $R_8$, $R_9$, $R_{10}$, $R_{11}$, $R_{12}$, $R_{13}$, $R_{14}$, $R_{15}$, $R_{16}$, $R_{17}$, $R_{18}$, $R_{19}$, $R_{20}$, $R_{21}$, $R_{22}$, $R_{23}$, $R_{24}$, $R_{25}$, $R_{26}$, $R_{27}$, $R_{28}$, $R_{29}$, $R_{30}$, $R_{31}$ and $R_{32}$ represent independently one of H, $C_mH_{2m+1}$ (m=1 to 15), $OC_pH_{2p+1}$ (p=1 to 15), and n=1 to 4, and wherein $Y_1$ and $Y_2$ represent independently one of formula (19) to (34),

(19)
H

(20)
$C_iH_{2i+1}$

(21)
$OC_jH_{2j+1}$

(22)
$SC_kH_{2k+1}$

(23)
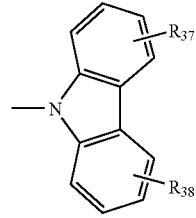

(24)
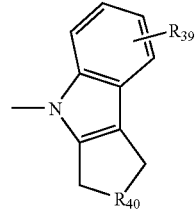

(25)
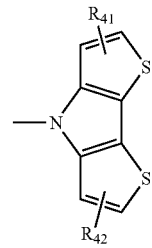

(26)
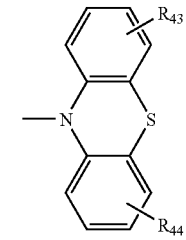

(27)
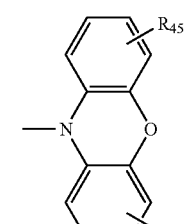

(28)
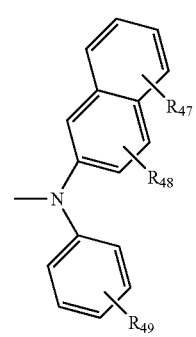

(29)
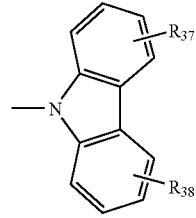

(30)
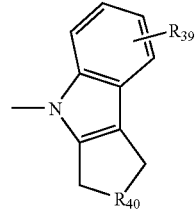

(31)
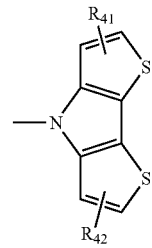

(32)
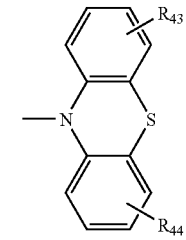

(33)
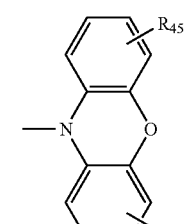

(34)
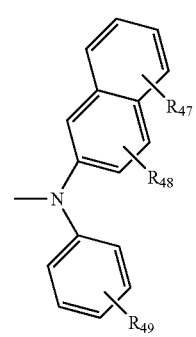

wherein, i=1 to 15 in formula (20), and j=1 to 15 in formula (21), and K=1 to 15 in formula (22), wherein $R_{33}$, $R_{34}$, $R_{35}$, $R_{36}$, $R_{39}$, $R_{41}$, $R_{42}$, $R_{43}$, $R_{44}$, $R_{45}$, $R_{46}$, $R_{47}$, $R_{48}$ and $R_{49}$ independently represent one of H, $C_mH_{2m+1}$ ($m=1\sim15$), $OC_pH_{2p+1}$ ($p=1\sim15$), wherein $R_{37}$, $R_{38}$ independently represent one of H or $C_mH_{2m+1}$ ($m=1\sim6$) or $OC_pH_{2p+1}$ ($p=1\sim6$), wherein $R_{40}$ represents $C_qH_{2q}$ ($q=1\sim3$), wherein $Z_1$ represents one of formula (35)~(37), (39) and (41) and $Z_2$ represents hydrogen or one of the formula (35) to (37), (39) and (41) or a group the same as $Z_1$,

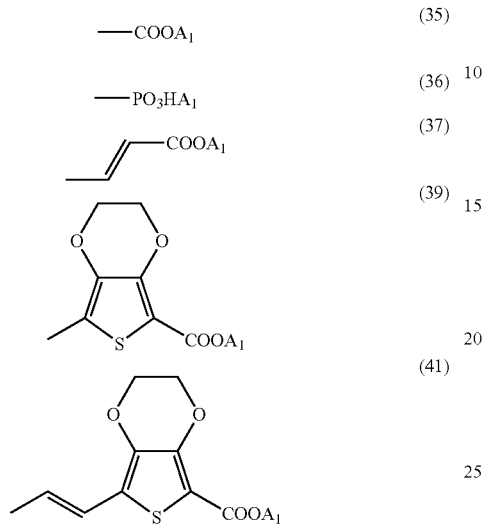

wherein $A_1$ represents hydrogen (H), lithium (Li), sodium (Na), potassium (K) or tetra-alkyl ammonium groups (represented by general formula (42))

(42)

wherein $R_{52}$, $R_{53}$, $R_{54}$, $R_{55}$ independently represent one of H, $C_mH_{2m+1}$ ($m=1$ to 15), and when $Z_1$ and $Z_2$ both represent formula (35) and $X_1$ represents one of the formula (2) to (4) and $X_2$ represents hydrogen, $Y_2$ does not represent one of the formula (19) to (21), and when $Z_1$ and $Z_2$ both represent formula (35) and $X_1$ and $X_2$ both represent one of formula the (2) to (4), $Y_2$ does not represent one of the formula (19) to (21).

* * * * *